(12) United States Patent
Thakur et al.

(10) Patent No.: US 11,338,145 B2
(45) Date of Patent: May 24, 2022

(54) CURRENT STEERING TO ACHIEVE SPATIAL SELECTIVITY FOR HIS BUNDLE PACING

(71) Applicant: Cardiac Pacemakers, Inc., St. Paul, MN (US)

(72) Inventors: Pramodsingh H. Thakur, Woodbury, MN (US); Allan C. Shuros, St. Paul, MN (US); Brian Soltis, St. Paul, MN (US); Juan G. Hincapie, Maple Grove, MN (US); Qi An, Blaine, MN (US); Yinghong Yu, Shoreview, MN (US); Keith R. Maile, New Brighton, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 16/250,715

(22) Filed: Jan. 17, 2019

(65) Prior Publication Data
US 2019/0217097 A1    Jul. 18, 2019

Related U.S. Application Data

(60) Provisional application No. 62/618,366, filed on Jan. 17, 2018.

(51) Int. Cl.
| | | |
|---|---|---|
| *A61N 1/36* | (2006.01) |
| *A61N 1/368* | (2006.01) |
| *A61N 1/375* | (2006.01) |
| *A61N 1/05* | (2006.01) |
| *A61N 1/362* | (2006.01) |

(52) U.S. Cl.
CPC .......... *A61N 1/3682* (2013.01); *A61N 1/056* (2013.01); *A61N 1/0573* (2013.01); *A61N 1/3627* (2013.01); *A61N 1/37512* (2017.08); *A61N 1/37518* (2017.08)

(58) Field of Classification Search
CPC .............. A61N 1/3682; A61N 1/37512; A61N 1/37518; A61N 1/056; A61N 1/0573; A61N 1/3627
USPC ............................................................ 607/17
See application file for complete search history.

(56) References Cited

U.S. PATENT DOCUMENTS

| | | | |
|---|---|---|---|
| 6,216,043 B1 * | 4/2001 | Swanson .............. | A61N 1/0565 607/122 |
| 6,771,996 B2 * | 8/2004 | Bowe ................. | A61B 18/1492 600/374 |
| 8,942,805 B2 | 1/2015 | Shuros et al. | |
| 9,381,361 B2 * | 7/2016 | Giovangrandi ........ | A61B 18/14 |
| 2010/0318147 A1 * | 12/2010 | Forslund .............. | A61N 1/0573 607/17 |

(Continued)

OTHER PUBLICATIONS

Deurloo, K. E. I. (1998). Transverse tripolar stimulation of peripheral nerve: a modelling study of spatial selectivity. Med. Biol. Eng. Comput., 36:66-74.

*Primary Examiner* — Amanda K Hulbert
(74) *Attorney, Agent, or Firm* — Faegre Drinker Biddle & Reath LLP

(57) ABSTRACT

Various aspects of the present disclosure are directed toward apparatuses, systems, and methods for pacing a HIS bundle of a patient. The apparatuses, systems, and methods may include applying stimulation energy through one or more of a plurality of electrodes to direct a stimulation locus and pace a HIS bundle of a patient.

18 Claims, 9 Drawing Sheets

(56) References Cited

U.S. PATENT DOCUMENTS

| | | | |
|---|---|---|---|
| 2012/0101539 A1* | 4/2012 | Zhu | A61N 1/0565 607/4 |
| 2014/0172035 A1* | 6/2014 | Shuros | A61N 1/365 607/18 |
| 2015/0005762 A1* | 1/2015 | Belk | A61B 18/1492 606/41 |
| 2016/0136430 A1 | 5/2016 | Moffitt et al. | |
| 2016/0136434 A1* | 5/2016 | Lee | A61N 1/3686 607/30 |
| 2017/0224414 A1* | 8/2017 | Weinkam | A61B 5/6853 |

\* cited by examiner

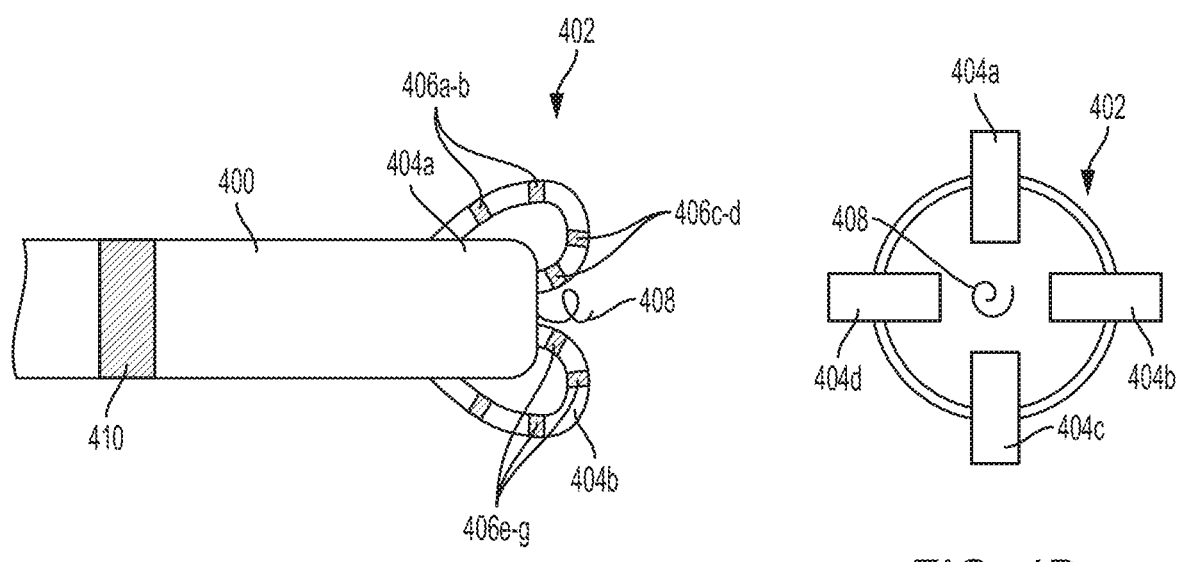

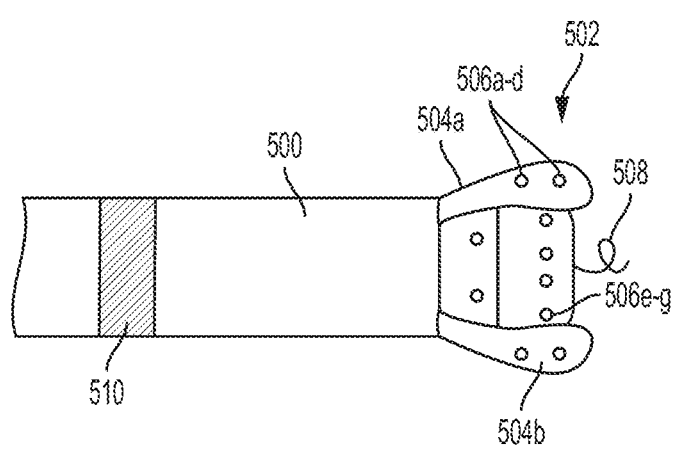 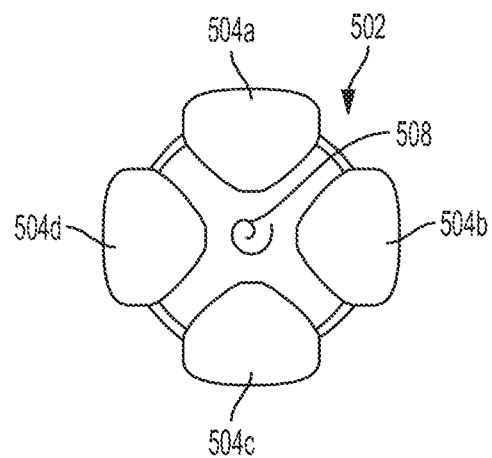
FIG. 5A
FIG. 5B

CURRENT STEERING TO ACHIEVE SPATIAL SELECTIVITY FOR HIS BUNDLE PACING

TECHNICAL FIELD

This application claims priority to Provisional Application No. 62/618,366, filed Jan. 17, 2018, which is herein incorporated by reference in its entirety.

TECHNICAL FIELD

The present invention relates to medical devices and methods for pacing a patient's heart. More specifically, the invention relates to devices and methods for selectively pacing a HIS bundle of the patient's heart.

BACKGROUND

Medical devices include devices designed to be implanted into a patient. Some examples of these implantable medical devices (IMDs) include cardiac function management (CFM) devices such as implantable pacemakers, implantable cardioverter defibrillators (ICDs), cardiac resynchronization therapy devices (CRTs), and devices that include a combination of such capabilities. The devices can be used to treat patients or subjects using electrical or other therapy or to aid a physician or caregiver in patient diagnosis through internal monitoring of a patient's condition. The devices may include one or more electrodes in communication with one or more sense amplifiers to monitor electrical heart activity within a patient.

Cardiac pacing may result in dyssynchronous ventricular contractions due to the slow propagation of electrical signals through myocardium tissue of the heart. His bundle pacing (HBP) may provide physiologic pacing by activating the intrinsic conduction system. However, the HIS bundle having small size/area increases the difficulty in effectively pacing the heart of a patient.

SUMMARY

In Example 1, an apparatus including: a plurality of electrodes arranged with a lead body; and an implantable medical device coupled to the plurality of electrodes and configured to apply stimulation energy through one or more of the plurality of electrodes to direct a stimulation locus and pace a HIS bundle of a patient.

In Example 2, the apparatus of Example 1, wherein the implantable medical device is configured to convey electrical energy to one or more of the plurality electrodes to stimulate a portion of the HIS bundle of the patient at the stimulation locus, analyze electrical signals via one or more of the plurality of electrodes in response to the conveyed electrical energy, and displace the stimulation locus based on analyzed signals to pace the HIS bundle of the patient.

In Example 3, the apparatus of any one of Examples 1-2, wherein a distal portion of the lead body is configured to facilitate placement of the lead body against a tissue wall about the HIS bundle.

In Example 4, the apparatus of Example 3, wherein the implantable medical device is configured to pace the HIS bundle of the patient based on a comparison of an electrical delay of an atrial-His bundle (AH) delay and a mechanical response of a portion of a heart of the patient.

In Example 5, the apparatus of Example 4, further including a sensor arranged with the lead body and configured to determine the mechanical response.

In Example 6, the apparatus of any one of Examples 1-5, wherein the distal portion of the lead body forms one of a ring and a spiral, and the plurality of electrodes are directed toward the tissue wall about the HIS bundle.

In Example 7, the apparatus of Example 6, wherein the distal portion of the lead body forms a spiral with the plurality of electrodes arranged with the spiral, and the lead body includes a bias portion configured to stabilize the plurality of electrodes of the spiral against the tissue wall of the HIS bundle.

In Example 8, the apparatus of any one of Examples 1-5, wherein the distal portion of the lead body includes one or more expandable tines, and the plurality of electrodes are arranged on the one or more expandable tines.

In Example 9, the apparatus of any one of Examples 1-5, wherein the distal portion of the lead body includes one or more wings extending outwardly from the distal portion relative to an end portion of the lead body, and the plurality of electrodes are arranged on at least one of the one or more wings and the end portion of the lead body.

In Example 10, the apparatus of any one of Examples 1-5, wherein the distal portion of the lead body includes one or more expandable balloon portions, and the plurality of electrodes are arranged with the one or more expandable balloon portions.

In Example 11, the apparatus of any one of Examples 1-5, wherein an end portion of the lead body includes the plurality of electrodes, and the plurality of electrodes are segmented by an insulative material.

In Example 12, the apparatus of any one of Examples 1-11, further comprising a fixation helix arranged at a distal end of the lead body, the fixation helix configured to anchor the lead body to the tissue wall about the HIS bundle.

In Example 13, the apparatus of Example 12, wherein the fixation helix is one of the plurality of electrodes.

In Example 14, the apparatus of any one of Examples 1-13, further comprising an external programmer configured to receive signals from the implantable medical device, perform an analysis of the signals, and transmit at least one of a series of stimulation parameter sets to the implantable pulse to direct the stimulation locus and pace the HIS bundle of the patient.

In Example 15, the apparatus of Example 14, wherein the external programmer is configured to direct the stimulation locus in response to a user intervention.

In Example 16, an apparatus including: a plurality of electrodes; an implantable medical device coupled to the plurality of electrodes and configured to: convey electrical energy to one or more of the plurality of electrodes to stimulate a portion of a HIS bundle of a patient at a stimulation locus; analyze electrical signals via one or more of the plurality of electrodes in response to the conveyed electrical energy; and displace the stimulation locus based on the analyzed signals to pace the HIS bundle of the patient.

In Example 17, the apparatus of Example 16, further including a lead body coupled to the implantable medical device and the plurality of electrodes are arranged with the lead body, and wherein a distal portion of the lead body configured to facilitate placement of the lead body against a tissue wall about the HIS bundle.

In Example 18, the apparatus of Example 16, wherein the distal portion of the lead body forms one of a ring and a spiral, and the plurality of electrodes are directed toward a tissue wall about the HIS bundle.

In Example 19, the apparatus of Example 18, wherein the distal portion of the lead body forms a spiral with the plurality of electrodes arranged with the spiral, and the lead body includes a bias portion configured to stabilize the plurality of electrodes of the spiral against the tissue wall of the HIS bundle.

In Example 20, the apparatus of Example 16, wherein the distal portion of the lead body includes one or more expandable tines, and the plurality of electrodes are arranged on the one or more expandable tines.

In Example 21, the apparatus of Example 16, wherein the distal portion of the lead body includes one or more wings extending outwardly from the distal portion relative to an end portion of the lead body, and the plurality of electrodes are arranged on at least one of the one or more wings and the end portion of the lead body.

In Example 22, the apparatus of Example 16, wherein the distal portion of the lead body includes one or more expandable balloon portions, and the plurality of electrodes are arranged with the one or more expandable balloon portions.

In Example 23, the apparatus of Example 16, wherein an end portion of the lead body includes the plurality of electrodes, and the plurality of electrodes are segmented by an insulative material.

In Example 24, the apparatus of Example 16, further comprising a fixation helix arranged at a distal end of the lead body, the fixation helix configured to anchor the lead body to the tissue wall about the HIS bundle.

In Example 25, the apparatus of Example 24, wherein the fixation helix is one of the plurality of electrodes.

In Example 26, the apparatus of Example 16, wherein the implantable medical device is configured to pace the HIS bundle of the patient based on a comparison of an electrical delay of an atrial-His bundle (AH) delay and a mechanical response of a portion of a heart of the patient.

In Example 27, the apparatus of Example 26, further comprising a lead body coupled to the implantable medical device and a sensor arranged with the lead body, and the sensor is configured to determine the mechanical response.

In Example 28, a system including: a plurality of electrodes; an implantable medical device coupled to the plurality of electrodes and configured to convey electrical energy to one or more of the plurality of electrodes to stimulate a portion of a HIS bundle of a patient at a stimulation locus and displace the stimulation locus to pace a HIS bundle of a patient; and an external programmer configured to receive the signals from the implantable medical device, analyze electrical signals via one or more of the plurality of electrodes in response to the conveyed electrical energy and transmit stimulation parameters to the implantable medical device to define the displacement of the stimulation locus.

In Example 29, the system of Example 28, wherein the plurality of electrodes are separated by an insulative material to direct the electrical energy toward the HIS bundle of the patient.

In Example 30, the system of Example 28, wherein the distal portion of the lead body forms a curvature, and the distal portion includes a bias configured to stabilize the plurality of electrodes against a tissue wall of the HIS bundle.

In Example 31, the system of Example 28, wherein the distal portion of the lead body includes one or more expandable portions, and the plurality of electrodes are arranged on the one or more expandable portions.

In Example 32, the system of Example 28, wherein the expandable portions include at least one of expandable tines, expandable wings, and an expandable balloon.

In Example 33, a method of pacing a HIS bundle of a patient, the method including: arranging a plurality of electrodes at a HIS bundle of a patient; conveying electrical energy to one or more of the plurality of electrodes to stimulate a portion of the HIS bundle of the patient at a stimulation locus; analyzing electrical signals via one or more of the plurality of electrodes in response to the conveyed electrical energy; and displacing the stimulation locus based on the analyzed signals to pace the HIS bundle of the patient.

In Example 34, the method of Example 33, further including a lead body coupled to the implantable medical device and the plurality of electrodes are arranged with the lead body and further including directing the plurality of electrodes to apply the stimulation energy toward the HIS bundle using at least one of insulative material on the lead body and expandable portions arranged at a distal portion of the lead body.

In Example 35, the method of Example 34, wherein the expandable portions include at least one of expandable tines, expandable wings, and an expandable balloon, and wherein the plurality of electrodes are arranged with the expandable portions.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 4A shows a side view of a portion of an example lead and electrodes that can be used in relation to embodiments of the present invention.

FIG. 4B shows an end view of the portion of the example lead and electrodes, as shown in FIG. 4A.

FIG. 5A shows a side view of a portion of another example lead and electrodes that can be used in relation to embodiments of the present invention.

FIG. 5B shows an end view of the portion of the example lead and electrodes, as shown in FIG. 5A.

Figure 1:
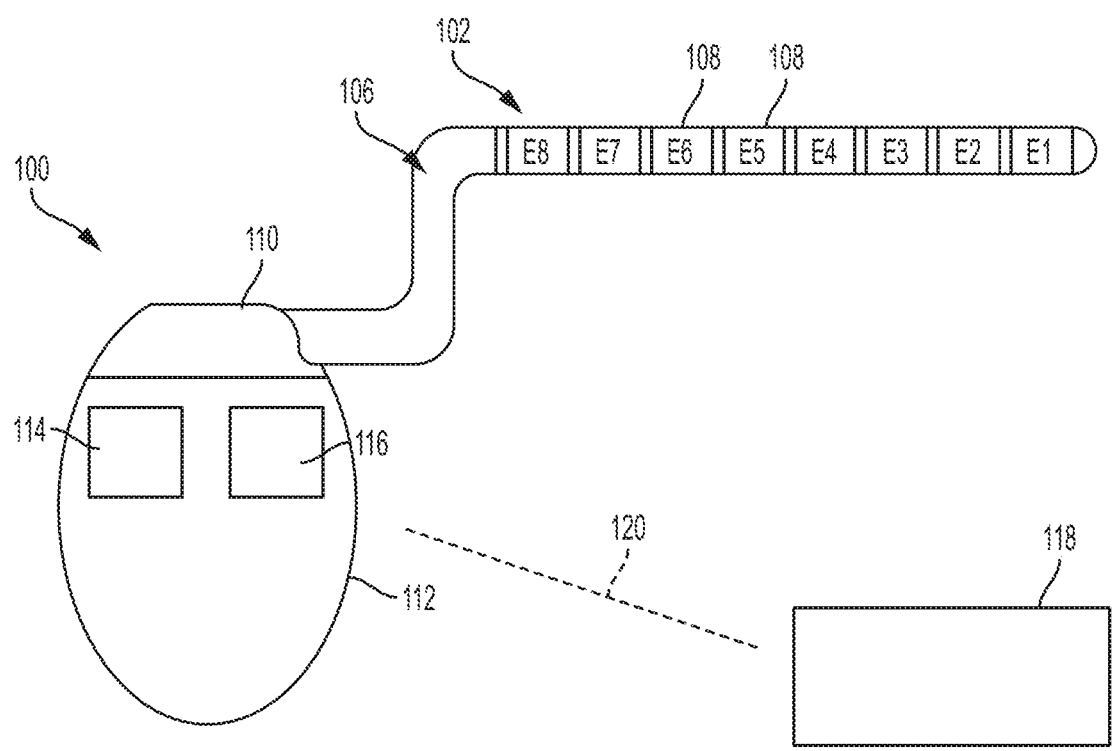
FIG. 1 shows an example implantable medical device that can be used in relation to embodiments of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

As the terms are used herein with respect to ranges of measurements (such as those disclosed immediately above), "about" and "approximately" may be used, interchangeably, to refer to a measurement that includes the stated measurement and that also includes any measurements that are reasonably close to the stated measurement, but that may differ by a reasonably small amount such as will be understood, and readily ascertained, by individuals having ordinary skill in the relevant arts to be attributable to measurement error, differences in measurement and/or manufacturing equipment calibration, human error in reading and/or setting measurements, adjustments made to optimize performance and/or structural parameters in view of differences in measurements associated with other components, particular implementation scenarios, imprecise adjustment and/or manipulation of objects by a person or machine, and/or the like.

Although the term "block" may be used herein to connote different elements illustratively employed, the term should not be interpreted as implying any requirement of, or particular order among or between, various steps disclosed herein unless and except when explicitly referring to the order of individual steps. Additionally, a "set" or "group" of items (e.g., inputs, algorithms, data values, etc.) may include one or more items, and, similarly, a subset or subgroup of items may include one or more items.

DETAILED DESCRIPTION

Various aspects of the present disclosure are directed toward apparatuses, systems and methods of HIS bundle pacing. Conventional cardiac pacing may result in dyssynchronous ventricular contractions because of the slow propagation through working myocardium. His bundle pacing (HBP) can provide physiologic pacing by activating the intrinsic conduction system. The His bundle is composed of Purkinje fibers organized in a longitudinal orientation that are predestined to terminate peripherally in the ventricles.

In patients with, for example, a block of left bundle branch (e.g., a left bundle branch block or LBBB), the impediment can located be in the HIS bundle. His bundle pacing, in certain instances, can correct bundle branch block by recruiting previously latent conduction fibers in the HIS bundle (e.g., in the Cardiac Resynchronization Therapy (CRT) population). This HIS bundle is a small area (2 mm by 2 mm) that has previously required mapping using multi-electrode catheters prior to implantation of a stimulation lead. The various aspects of the present disclosure are directed toward directing stimulation energy to one or more electrodes to pace the HIS bundle. The displacement of stimulation energy across the electrodes allows for targeting of the HIS bundle without the need for physical arrangement of a lead to find a stimulation location, which may be time consuming. Directing stimulation energy also lessens the need for potential replacing of leads as there is no guarantee that the targeting simulation location will hold chronically as the lead interface matures. Directing stimulation energy provides spatially selective HIS pacing after implantation of the lead.

FIG. 1 shows an example implantable medical device 100 that can be used in relation to embodiments of the present invention. The implantable medical device 100 may be coupled to lead 102 in accordance with embodiments of the disclosure. The lead 102 may include a lead body 106. The lead 102 includes a number of electrodes 108 arranged on the lead body 106. The electrodes 108 may be arranged circumferentially around the lead 102 as ring electrodes mounted around the lead body 106. In embodiments, the electrodes 108 may extend at least approximately around the circumference of the lead body 106. In embodiments, one or more of the electrodes 108 may extend partially around the circumference of the lead body 106. In some instances, for example, the plurality of electrodes 108 may be segmented electrodes that are circumferentially and axially disposed about the lead body 106. Each of the plurality of illustrated electrodes 108 are labeled E1-E8, however the actual number and shape of leads and electrodes vary according to the application.

As shown, the lead 102 is operatively coupled to the implantable medical device 100. A connector/header 110 arranged with the implantable medical device 100 couples an end of the lead 102 to the implantable medical device 100, thereby operatively (e.g., communicatively, electrically, and/or physically) coupling the electrodes 108 to the internal electronics within the implantable medical device 100. In embodiments, the implantable medical device 100 may be configured to communicate wirelessly with one or more leads 102, in which case, the implantable medical device 100 may include one or more wireless communication antennas, coils, and/or the like. The implantable medical device 100 may also include a housing 112, which contains and houses electronic and other components. In embodiments, the implantable medical device 100 may include a pulse generator that may be implantable within a patient (e.g., an implantable pulse generator (IPG)), or may be configured to be positioned external to the patient. In instances, the housing 112 may be formed of an electrically conductive, biocompatible material, such as titanium, and may form a hermetically sealed compartment wherein the internal electronics are protected from the body tissue and fluids.

The housing 112 may enclose sensing circuitry 114 configured to receive, from one or more of the electrodes 108, physiological signals obtained by the one or more electrodes 108. The housing 112 may also enclose pulse generation circuitry 116 that delivers stimulation energy via one or more of the electrodes 108. According to various embodiments, the sensing circuitry 114 (or aspects thereof) and/or the pulse generation circuitry 116 (or aspects thereof) may be configured to be implanted in the patient and/or disposed external to the patient. That is, for example, in embodiments, the sensing circuitry 114 and the pulse generation circuitry 116 may be integrated within a processor disposed in an implantable medical device (e.g., the implantable medical device 100) and/or an external medical device. The sensing circuitry 114 (or aspects thereof) and/or the pulse generation circuitry 116 (or aspects thereof) may be implemented in any combination of hardware, firmware, and software. For example, the sensing circuitry 114 may be, or include, a first algorithm, virtual processor, and/or process implemented by a processor, and, similarly, the pulse generation circuitry 116 circuit may be, or include, a second algorithm, virtual processor, and/or process implemented by a processor. In embodiments, the sensing circuitry 114 may be, or include, a first set of physical and/or virtual circuit elements, and, similarly, the pulse generation circuitry 116 may be, or include, a second set of physical and/or virtual circuit elements.

In some embodiments, the implantable medical device 100 may include a programmable micro-controller or microprocessor, and may include one or more programmable logic devices (PLDs) or application specific integrated circuits (ASICs). In some implementations, the implantable medical device 100 may include memory as well. Although the present implantable medical device 100 having a microprocessor-based architecture, it will be understood that the implantable medical device 100 (or other device) may be implemented in any logic-based integrated circuit architecture, if desired. The implantable medical device 100 may include digital-to-analog (D/A) converters, analog-to-digital (A/D) converters, timers, counters, filters, switches, and/or the like.

The sensing circuitry 114 may be configured to receive a physiological signal obtained by one or more of the electrodes 108, and analyze the received physiological signal to identify a stimulation or therapy region. According to embodiments, the physiological signal may include intrinsic electrical activity, a physiological response to an applied stimulation signal, and/or the like. For example, the sensing circuitry 114 may be configured to obtain a physiological signal that is a response to a stimulation signal administered using one or more of the electrodes 108, and to analyze that signal to identify a therapy location. One or more of the electrodes 108 supply a stimulation signal, while adjacent ones of the selected electrodes 108 obtain the physiological signal that is a response to a stimulation signal. In embodiments, the sensing circuitry 114 may be configured to evaluate motion of the patient, electrical activity of the heart, and/or other physiological signals to identify a therapy region.

The stimulation energy may be in the form of a pulsed electrical waveform to one or more of the electrodes 108 in accordance with a set of stimulation parameters, which may be programmed into the implantable medical device 100, transmitted to the implantable medical device 100, and/or the like. Stimulation parameters may include, for example, electrode combinations that define the electrodes that are activated as anodes (positive), cathodes (negative), turned on, turned off (zero), percentage of stimulation energy assigned to each electrode (fractionalized electrode configurations), and/or electrical pulse parameters, which define the pulse amplitude (measured in milliamps or volts depending on whether the implantable medical device 100 supplies constant current or constant voltage to one or more of the electrodes 108), pulse duration (measured in microseconds), pulse rate (measured in pulses per second), pulse waveform, and/or burst rate (measured as the stimulation on duration X and stimulation off duration Y). The pulse generation circuitry 116 may be capable of delivering the stimulation energy to the one or more of the electrodes 108 over multiple channels or over only a single channel. Stimulation energy may be used to identify therapy regions and/or to provide stimulation therapy to identified therapy regions or alter therapy regions over time to prevent exhaustion in one location.

Stimulation energy may be transmitted to the tissue in a multipolar (e.g., bipolar, tripolar, etc.) fashion. Bipolar stimulation, a type of multipolar stimulation, occurs when two of the electrodes 108 are activated as anode and cathode, so that stimulation energy is transmitted between the activated electrodes. Multipolar stimulation also may occur when more than two (e.g., three, four, etc.) of the electrodes 108 are activated, e.g., two as anodes and a third as a cathode, or two as cathodes and a third as an anode. In certain instances, the pulse generation circuitry 116 may individually control the magnitude of electrical current flowing through each of the electrodes. In these instances, current generators may be used to supply current-regulated amplitudes to selectively generate independent current sources for one or more of the electrodes 108.

In certain instances, the implantable medical device 100 may be communicatively coupled to one or more external devices 118 (one external device 118 is shown for simplicity) and communicate via wireless signals 120. The external device 118 or external devices may be an IMD programmer, an external charger used to transcutaneously charge the implantable medical device via an inductive link over wireless signals 120, or other of external device. The implantable wireless signals 106 may be radio frequency (RF) or other telemetry signals. The external device(s) 118, in certain instances, may perform an analysis of the signals acquired by the plurality of electrodes 108. In addition, the sensed physiological information may be used to modify the stimulation parameters in accordance with which the implantable medical device 100 delivers electrical energy. In certain instances, the external device 118 may include a graphical user interface that visualizes the physiological signal (sensed in response to a stimulation signal administered using one or more of the electrodes 108) to assist in identifying a therapy location. The physician or user may select which one of the electrodes 108 deliver stimulation energy based on the visualization. In certain instances, the external device 118 may include a device (e.g., a joy stick or throttle) that allows for the physician to drive the stimulation to different ones of the electrodes 108.

As discussed in further detail below with reference to FIGS. 2-7, for example, the implantable medical device 100 may be configured to apply stimulation energy through one or more of the plurality of electrodes 108 to direct a stimulation locus and pace a HIS bundle of a patient. The plurality of electrodes 108 may be anchored to heart tissue and directly in contact with the HIS bundle. The HIS bundle is a spatially small location to acquire signals from and to stimulate. Directing the stimulation locus for the energy applied to pace the HIS bundle provides targeted stimulation of the HIS bundle.

The illustrative components shown in FIG. 1 are not intended to suggest any limitation as to the scope of use or functionality of embodiments of the disclosed subject matter. Neither should the illustrative components be interpreted as having any dependency or requirement related to any single component or combination of components illustrated therein. Additionally, any one or more of the components depicted in any of the FIG. 1 may be, in embodiments, integrated with various other components depicted therein (and/or components not illustrated), all of which are considered to be within the ambit of the disclosed subject matter. For example, the external device(s) 118 may be used in connection with leads and electrodes discussed with reference to FIGS. 2-7. Similarly, the His bundle pacing timing optimization, discussed with reference to FIG. 9, may be used in connection with the implantable medical device 100.

Figure 2:
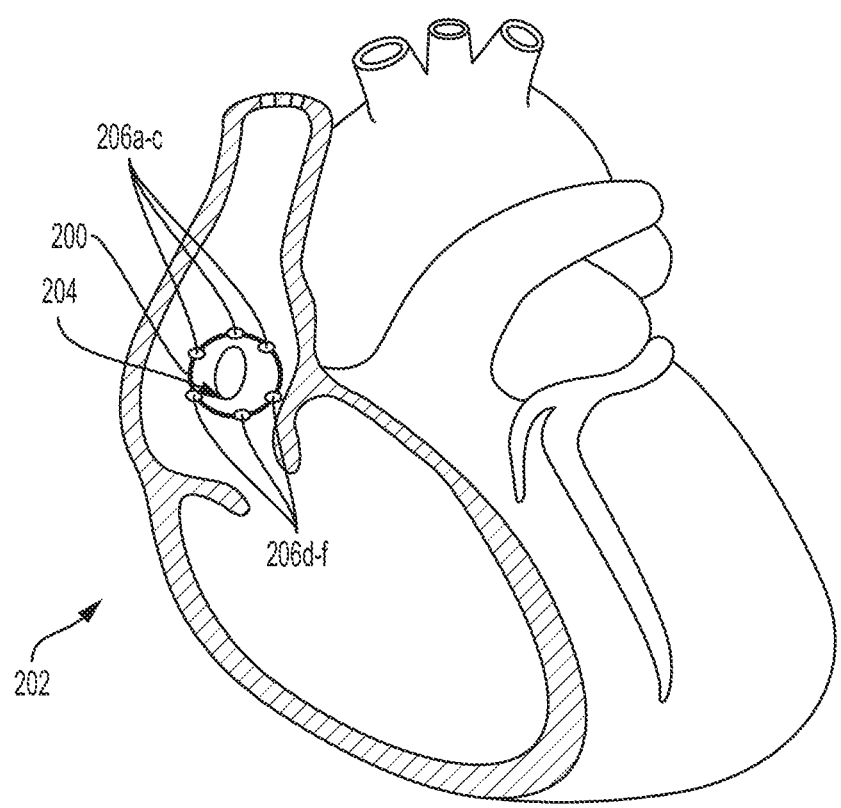
FIG. 2 shows a portion of example lead and electrodes that can be used in relation to embodiments of the present invention.

FIG. 2 shows a portion of example lead body and electrodes that can be used in relation to embodiments of the present invention. An end portion 200 of the lead is shown in FIG. 2 arranged within a patient's heart 202. The end portion 200 is circular and may be a closed loop, in certain instances. The circular end portion 200 may be arranged within the heart 202 at the patient's HIS bundle 204.

As also shown in FIG. 2, the circular end portion 200 includes a plurality of electrodes 206a-f. The electrodes 206a-f may be arranged uniformly about a circumference of the circular end portion 200. In certain instances, the electrodes 206a-f are directed toward an exterior surface of the circular end portion 200. In this manner, signals acquired by and stimulation applied by the electrodes 206a-f may be routed in a specific direction. In certain instances, the circular end portion 200 may be arranged to facilitate placement of the circular end portion 200 of the lead body against a tissue wall about the HIS bundle 204. More specifically, the electrodes 206a-f are directed against and face the tissue wall of the HIS bundle 204.

The circular end portion 200 may be formed of an insulative material in order to electrically isolate the electrodes 206a-f from one another. In addition, the insulative material may be arranged such that the electrodes 206a-f insulate signals from being acquired or delivered from certain surfaces of the circular end portion 200. More specifically, energy resulting from activated ones of the electrodes 206a-f or acquired by the electrodes 206a-f is directed toward the HIS bundle 204. The insulative material may be Pebax, Polyethelene (Low or high density), or polyurethane.

As noted above with reference to FIG. 1, the electrodes 206a-f may be coupled to an implantable medical device (e.g., which also may be coupled to external devices as described above). The implantable medical device may be configured to: convey electrical energy to one or more of the electrodes 206a-f to stimulate a portion of the HIS bundle 204 of a patient at a stimulation locus. The implantable medical device may also analyze electrical signals via one or more of the plurality of electrodes 206a-f in response to the conveyed electrical energy, and displace the stimulation locus based on the analyzed signals to pace the HIS bundle 204 of the patient.

The locus of the stimulation region may be electronically displaced in any one of a variety of manners. In certain instances, different combinations of the electrodes 206a-f may be selected to direct the stimulation locus within the circular end portion 200 across the HIS bundle 204. One or more of the electrodes 206a-f may be activated the apply stimulation and direct the stimulation locus toward the activated ones of the electrodes 206a-c. For example, the number and which of the electrodes 206a-f are activated directs the stimulation locus. One of the electrodes 206a-f in the circular end portion 200 may be set to a "+" polarity (i.e., as an anode) and another electrode in the electrodes 206a-f in the circular end portion 200 is set to a "−" polarity (i.e., as a cathode). This polarity and grouping causes electrical current to flow from the electrodes 206a-f to the other of the electrodes 206a-f in a bipolar fashion, which results in the location of the single stimulation region between selected electrodes of the electrodes 206a-f.

As another example, if electrodes 206a-f are activated, the stimulation locus will be directed toward the portion of the circular end portion 200 at which the electrodes 206a-f are arranged. If electrodes 206e-f are activated, the stimulation locus will be directed toward the portion of the circular end portion 200 at which the electrodes 206e-f are arranged. Other combinations of the electrodes 206a-f, including bipolar, tripolar and additional combinations, can be selected to electronically displace the locus of the stimulation region within the circular end portion 200, which surrounds the HIS bundle 204. In certain instances, the electrodes 206a-f may be fractionally activated with the electrodes 206a-f partially activated as partial anodes or partial cathodes to focus the stimulation locus within the circular end portion 200 in a displaced relative to the amount the selected electrodes 206a-f are fractionalized. In addition, the amount of stimulation energy (e.g., current) driven to the selected electrodes 206a-f, by the implantable medical device, may control the depth at which the HIS bundle 204 is stimulated.

Figure 3:
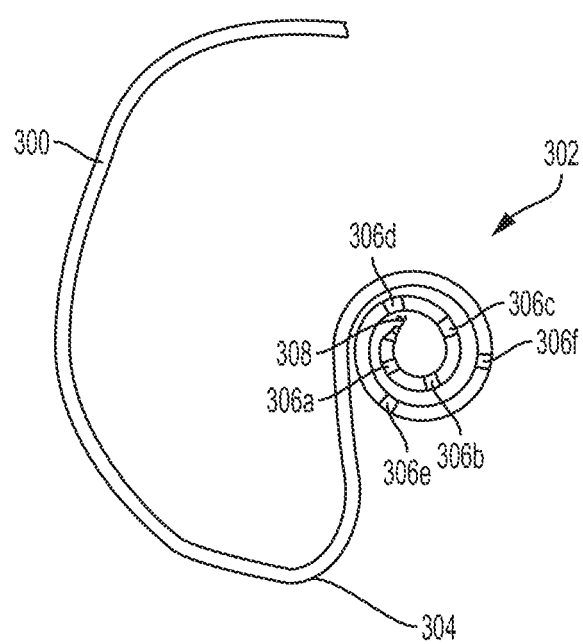
FIG. 3 shows a portion of another example lead and electrodes that can be used in relation to embodiments of the present invention.

FIG. 3 shows a portion of another example lead and electrodes that can be used in relation to embodiments of the present invention. As shown in FIG. 3, a lead body 300 includes a distal end portion 302 that forms a curvature. The curvature of the end portion 302 shown in FIG. 3 is a spiral shape. The spiral end portion 302 includes a plurality of electrodes 306a-f arranged and spaced about the spiral end portion 302. In certain instances, the plurality of electrodes 306a-f may be equally spaced about the spiral end portion 302.

In certain instances, the spiral end portion 302 of the lead body 300 is configured to facilitate placement of the lead body 300 against a tissue wall about the HIS bundle. The lead body 300, which is coupled to an implantable medical device, includes a bias curve portion 304 that loops opposite an atrial wall of the patient's heart and pushes the spiral end portion 302 against the septum for stabilization. The bias curve portion 304 may direct and stabilize the spiral end portion 302 against the HIS bundle of the patient. The spiral end portion 302 may force one or more of the electrodes 306a-f to directly contact the HIS bundle of the patient.

In certain instances, the distal end of the lead body 300 includes a fixation helix 308. The fixation helix 308 is configured to anchor the lead body to the tissue wall about the HIS bundle. In addition, the fixation helix 308 may function as an electrode and may penetrate the tissue wall to directly contact the HIS bundle. In certain instances, one or more of the electrodes 306a-f may include a similar mechanism to penetrate tissue. In these instances, the electrodes 306a-f may only penetrate tissue and in other instances, the electrodes 306a-f may also anchor the lead body 300 within the tissue similar to the fixation helix 308.

The electrodes 306a-f (and the lead body 300) may be coupled to an implantable medical device that is configured to apply stimulation energy through one or more of the electrodes 306a-f (including the fixation helix 308) to direct a stimulation locus and pace a HIS bundle of a patient. In certain instances, the implantable medical device is configured to obtain a physiological signal that is a response to a stimulation signal administered using one or more of the electrodes 306a-f and/or the fixation helix 308, and to analyze that signal to identify a therapy location. One or more of the electrodes 306a-f and/or the fixation helix 308 supply a stimulation signal, while other ones of the selected electrodes 306a-f and/or the fixation helix 308 obtain the physiological signal that is a response to a stimulation signal.

Stimulation energy may be transmitted to the tissue in a multipolar (e.g., bipolar, tripolar, etc.) fashion. The implantable medical device may also analyze electrical signals via one or more of the plurality of electrodes 306a-f in response to the conveyed electrical energy, and displace the stimulation locus based on the analyzed signals to pace the HIS bundle of the patient. In this manner, the signals from the HIS bundle are acquired signals in order to direct the stimulation locus for the energy applied to pace the HIS bundle and provide targeted stimulation of the HIS bundle. The displacement of stimulation energy across the electrodes 306a-f allows for targeting of the HIS bundle without the need for physical re-arrangement of the lead body 300 to find a desired stimulation location. In certain instances, electrodes 306a-f are chosen to selectively stimulate the HIS bundle without stimulating areas outside of the HIS bundle such that the tissue of only the HIS bundle is activated. In other instances, electrodes 306a-f may be chosen to stimulate both the tissue of the HIS bundle and surrounding tissue area(s).

The lead body 300 may be flexible with the electrodes 306a-f being configured to expand after being arranged at the HIS Bundle (e.g., formed of an self-expanding material such as Nitinol or similar material for expansion). In addition, the electrodes 306a-f and/or the fixation helix 308 may be coated with a material such as Iridium oxide, Iridium, titanium nitride (TiN), or other similar conductive and biologically inert metals. The electrodes 306a-f may be a smooth metal or a mesh or may include three-dimensional structuring (e.g., pores, ridges, or surface roughness) to provide micro contacts. The electrodes 306a-f may be printed onto the lead body 300.

FIG. 4A shows a side view of a portion of an example lead and electrodes that can be used in relation to embodiments of the present invention. As shown in FIG. 4A, a lead body 400 includes a distal end portion 402 having expandable portions. The expandable portions shown in FIGS. 4A-B are expandable tines 404. In addition, a plurality of electrodes 406a-g are arranged with the expandable tines 404a-d. The expandable tines 404a-d are arranged at the distal end portion 402 of the lead body 400. Any number of tines 404a-d may be arranged at the distal end portion 402 of the lead body 400.

The tines 404a-d may direct and stabilize the distal end portion 402 and the electrodes 406a-g against a HIS bundle of a patient. The tines 404a-d may be configured to expand outwardly and lay flat against the tissue of the patient. In this manner, the electrodes 406a-g arranged with the tines 404a-d may span the area of the HIS bundle. In addition, tines 404a-d may be formed of an insulative material to direct electrical energy provided through the electrodes 406a-g toward the HIS bundle of the patient. In certain instances, the tines 404a-d are biased to press against the tissue wall and hold the lead body 400 in place. The tines 404a-d, after deployment of the lead body 400 (e.g., by way of a delivery sheath), are biased to fold outwardly from the configuration shown in FIG. 4A.

The electrodes 406a-g (and the lead body 400) may be coupled to an implantable medical device that is configured to apply stimulation energy through one or more of the electrodes 406a-g to direct a stimulation locus and pace the HIS bundle of a patient. In certain instances, the implantable medical device is configured to obtain a physiological signal that is a response to a stimulation signal administered using one or more of electrodes 406a-g, and to analyze that signal to identify a therapy location. One or more of electrodes 406a-g supply a stimulation signal, while other ones of electrodes 406a-g obtain the physiological signal that is a response to a stimulation signal.

Stimulation energy may be transmitted to the tissue in a multipolar (e.g., bipolar, tripolar, etc.) fashion. The implantable medical device may also analyze electrical signals via one or more of the plurality of electrodes 406a-g in response to the conveyed electrical energy, and displace the stimulation locus based on the analyzed signals to pace the HIS bundle of the patient. In this manner, the signals from the HIS bundle are acquired signals in order to direct the stimulation locus for the energy applied to pace the HIS bundle and provide targeted stimulation of the HIS bundle. The displacement of stimulation energy across the electrodes 406a-g allows for targeting of the HIS bundle without the need for physical re-arrangement of the lead body 400 to find a desired stimulation location. In certain instances, the lead body 400 may also include a lead body electrode 410 configured to function as an anode.

In certain instances, the distal end 402 of the lead body 400 includes a fixation helix 408. The fixation helix 408 is configured to anchor the lead body to the tissue wall about the HIS bundle. In addition, the fixation helix 408 may function as one of the electrodes and may similarly deliver and/or receive electrical signals. In certain instances, one or more of the electrodes 406a-g may include a similar mechanism to penetrate tissue. In these instances, the electrodes 406a-g may only penetrate tissue and in other instances, the electrodes 406a-g may also anchor the lead body 400 within the tissue similar to the fixation helix 408. In certain instances, one or more of the electrodes 406a-g may include a similar mechanism to penetrate tissue. In these instances, the electrodes 406a-g may only penetrate tissue and in other instances, the electrodes 406a-g may also anchor the lead body 300 within the tissue similar to the fixation helix 408.

FIG. 4B shows an end view of the portion of the example lead and electrodes, as shown in FIG. 4A. As shown in FIG. 4B, the tines 404a-d are circumferentially distributed about the end portion 402 of the lead body 400.

FIG. 5A shows a side view of a portion of another example lead and electrodes that can be used in relation to embodiments of the present invention. As shown in FIG. 5A, a lead body 500 includes a distal end portion 502 having expandable portions. The expandable portions shown in FIGS. 5A-B are expandable wings 504a-d. In addition, a plurality of electrodes 506a-g are arranged with the expandable wings 504a-d. Ones of the electrodes 506a-g may also be arranged with the distal end portion 502 of the lead body 500.

The expandable wings 504 may direct and stabilize the distal end portion 502 and the electrodes 506a-g against a HIS bundle of a patient. The expandable wings 504a-d may be configured to expand outwardly and lay flat against the tissue of the patient. The expandable wings 504a-d may be flexible to conform to the tissue. The electrodes 506a-g arranged with the tines 504a-d and/or the distal end 502 may span the area of the HIS bundle. In certain instances, the expandable wings 504a-d are configured to press against the tissue wall and hold the lead body 500 in place.

In certain instances, the distal end of the lead body 500 includes a fixation helix 508. The fixation helix 508 is configured to embed into the tissue and anchor the lead body to the tissue wall. In addition, the fixation helix 508 may function as an electrode. Additional electrodes may penetrate the tissue and be in direct contact with the HIS bundle and may or may not serve as anchoring mechanisms.

The electrodes 506a-g (and the lead body 500) may be coupled to an implantable medical device that is configured to apply stimulation energy through one or more of the electrodes 506a-g to direct a stimulation locus and pace the HIS bundle of a patient. In certain instances, the implantable medical device is configured to obtain a physiological signal that is a response to a stimulation signal administered using one or more of electrodes 506a-g, and to analyze that signal to identify a therapy location. One or more of electrodes 506a-g supply a stimulation signal, while other ones of electrodes 506a-g obtain the physiological signal that is a response to a stimulation signal. In certain instances, the lead body 500 may also include a lead body electrode 510 configured to function as an anode.

Stimulation energy may be transmitted to the tissue in a multipolar (e.g., bipolar, tripolar, etc.) fashion. The implantable medical device may also analyze electrical signals via one or more of the plurality of electrodes 506a-f in response to the conveyed electrical energy, and displace the stimulation locus based on the analyzed signals to pace the HIS bundle of the patient. In this manner, the signals from the HIS bundle are acquired signals in order to direct the stimulation locus for the energy applied to pace the HIS bundle and provide targeted stimulation of the HIS bundle. The displacement of stimulation energy across the electrodes 506a-f allows for targeting of the HIS bundle without the need for physical re-arrangement of the lead body 500 to find a desired stimulation location.

FIG. 5B shows an end view of the portion of the example lead and electrodes, as shown in FIG. 5A. As shown in FIG. 5B, the expandable wings 504a-d are circumferentially distributed about the end portion 502 of the lead body 500 and extend outwardly therefrom.

Figures 6A, 6B:
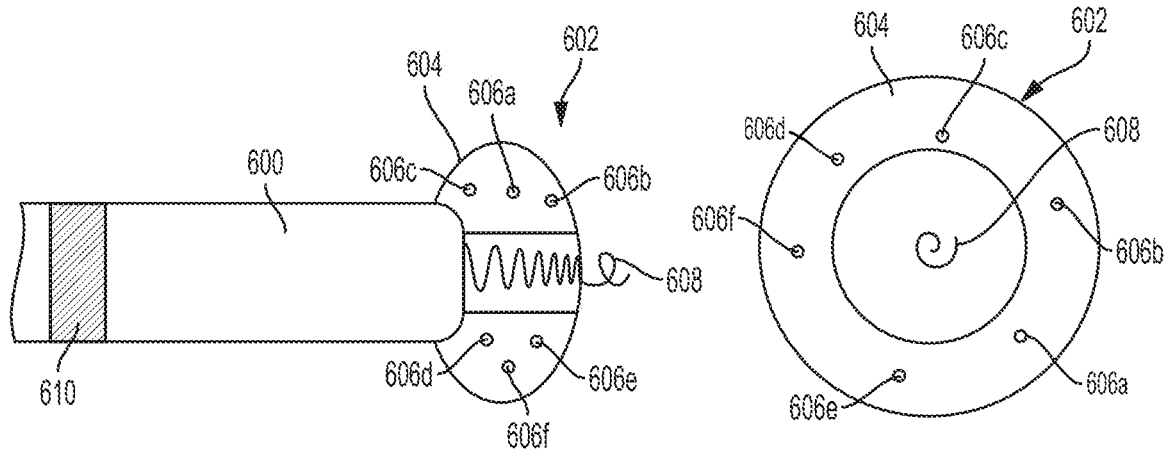
FIG. 6A shows a side view of a portion of another example lead and electrodes that can be used in relation to embodiments of the present invention.
FIG. 6B shows an end view of the portion of the example lead and electrodes, as shown in FIG. 6A.

FIG. 6A shows a side view of a portion of another example lead and electrodes that can be used in relation to embodiments of the present invention. FIG. 6B shows an end view of the portion of the example lead and electrodes, as shown in FIG. 6A. As shown in FIGS. 6A-B, a lead body 600 includes a distal end portion 602 having expandable portions. The expandable portions shown in FIGS. 6A-B are an expandable balloon 604. In addition, a plurality of electrodes 606a-f are arranged with the expandable balloon 604. The expandable balloon 604 is arranged to extend outwardly from the distal end portion 602 of the lead body. In addition, the distal end portion 602 of the lead body 600 may include a fixation helix 608 that extends through a central passageway or opening in the expandable balloon 604. The fixation helix 608 is configured to anchor the lead body to the tissue wall about the HIS bundle. In addition, the fixation helix 608 may function as an electrode.

The electrodes 606a-g (and the lead body 600) may be coupled to an implantable medical device that is configured to apply stimulation energy through one or more of the electrodes 606a-g to direct a stimulation locus and pace the HIS bundle of a patient. In certain instances, the implantable medical device is configured to obtain a physiological signal that is a response to a stimulation signal administered using one or more of electrodes 606a-g, and to analyze that signal to identify a therapy location. One or more of electrodes 606a-g supply a stimulation signal, while other ones of electrodes 606a-g obtain the physiological signal that is a response to a stimulation signal. In certain instances, the lead body 600 may also include a lead body electrode 610 configured to function as an anode.

Stimulation energy may be transmitted to the tissue in a multipolar (e.g., bipolar, tripolar, etc.) fashion. The implantable medical device may also analyze electrical signals via one or more of the plurality of electrodes 606a-g in response to the conveyed electrical energy, and displace the stimulation locus based on the analyzed signals to pace the HIS bundle of the patient. In this manner, the signals from the HIS bundle are acquired signals in order to direct the stimulation locus for the energy applied to pace the HIS bundle and provide targeted stimulation of the HIS bundle. The displacement of stimulation energy across the electrodes 606a-g allows for targeting of the HIS bundle without the need for physical re-arrangement of the lead body 600 to find a desired stimulation location. The expandable balloon 604 may span the area of the HIS bundle and facilitate the electrodes 606a-g being placed against the tissue wall and holding against the tissue wall. In certain instances, electrodes 606a-g are chosen to selectively stimulate the HIS bundle without stimulating areas outside of the HIS bundle such that the tissue of only the HIS bundle is activated. In other instances, electrodes 606a-g may be chosen to stimulate both the tissue of the HIS bundle and surrounding tissue area(s).

Figure 7A:
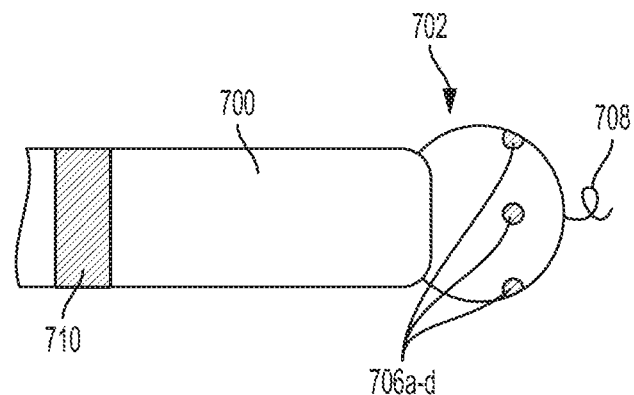
FIG. 7A shows a side view of a portion of another example lead and electrodes that can be used in relation to embodiments of the present invention.
Figure 7B:
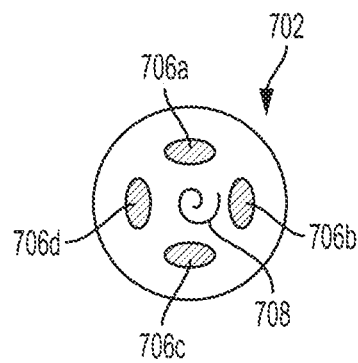
FIG. 7B shows an end view of the portion of the example lead and electrodes, as shown in FIG. 7A, in a first arrangement.
Figure 7C:
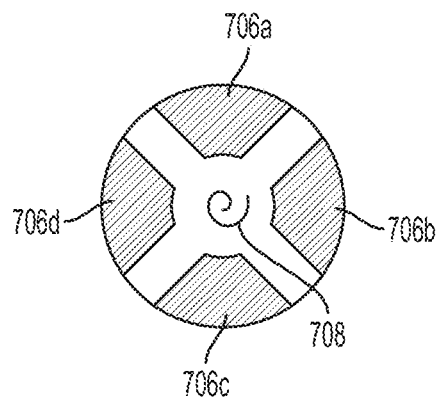
FIG. 7C shows an end view of the portion of the example lead and electrodes, as shown in FIG. 7A, in a second arrangement.

FIG. 7A shows a side view of a portion of another example lead and electrodes that can be used in relation to embodiments of the present invention. As shown in FIG. 7A, a lead body 700 includes a distal end portion 702 that is segmented. The segmented distal end portion 702 shown in FIGS. 7A-C includes a plurality of electrodes 706a-d segmented by an insulative material. The electrodes 706a-d may be electrodes printed or coated on the distal end portion 702 as shown in FIG. 7B in certain instances. In other instances, the electrodes 706a-d may be wedge electrodes embedded in or attached to the distal end portion 702, as shown in FIG. 7C. in addition, the distal end portion 702 may also include a fixation helix 708 centrally arranged about the electrodes 706a-d, which also may be configured to function as an electrode. The electrodes 706a-d and/or the fixation helix 708 may be formed of Iridium oxide, Iridium, titanium nitride (TiN), or other similar conductive and biologically inert metals. The electrodes 706a-d may be a smooth metal or a mesh or may include three-dimensional structuring (e.g., pores, ridges, or surface roughness) to provide micro contacts. The electrodes The insulative material used to form the segmented distal end portion 702 may be arranged such that the electrodes 706a-d insulate signals from being acquired or delivered from certain surfaces of the segmented distal end portion 702. More specifically, the segmented distal end portion 702 may insulate/isolate the electrodes 706a-d from signals in a proximal direction (e.g., opposite the HIS bundle). The insulative material may be Pebax, Polyethelene (low or high density), or polyurethane.

The electrodes 706a-d (and the lead body 700) may be coupled to an implantable medical device that is configured to apply stimulation energy through one or more of the electrodes 706a-d and/or the fixation helix 708 to direct a stimulation locus and pace the HIS bundle of a patient. In certain instances, the implantable medical device is configured to obtain a physiological signal that is a response to a stimulation signal administered using one or more of electrodes 706a-d and/or the fixation helix 708, and to analyze that signal to identify a therapy location. One or more of the electrodes 706a-d and/or the fixation helix 708 supply a stimulation signal, while other ones of the electrodes 706a-d and/or the fixation helix 708 obtain the physiological signal that is a response to a stimulation signal. In certain instances, the lead body 700 may also include a lead body electrode 710 configured to function as an anode.

Stimulation energy may be transmitted to the tissue in a multipolar (e.g., bipolar, tripolar, etc.) fashion. The implantable medical device may also analyze electrical signals via one or more of the plurality of electrodes 706a-f in response to the conveyed electrical energy, and displace the stimulation locus based on the analyzed signals to pace the HIS bundle of the patient. In this manner, the signals from the HIS bundle are acquired signals in order to direct the stimulation locus for the energy applied to pace the HIS bundle and provide targeted stimulation of the HIS bundle. The displacement of stimulation energy across the electrodes 706a-d and/or the fixation helix 708 allows for targeting of the HIS bundle without the need for physical re-arrangement of the lead body 700 to find a desired stimulation location.

The illustrative components shown in FIGS. 2-7 are not intended to suggest any limitation as to the scope of use or functionality of embodiments of the disclosed subject matter. Neither should the illustrative components be interpreted as having any dependency or requirement related to any single component or combination of components illustrated therein. Additionally, any one or more of the components depicted in any of the FIGS. 2-7 may be, in embodiments, integrated with various other components depicted therein (and/or components not illustrated), all of which are considered to be within the ambit of the disclosed subject matter. For example, the lead body and electrodes discussed with reference to FIGS. 2-7 may be used in connection with implantable medical device 100 and external device 118 shown and discussed with reference to FIG. 1. In addition, the electrodes discussed with reference to FIGS. 2-7 may be of any number (e.g., one, two, three, four, five, and so on).

Figure 8:
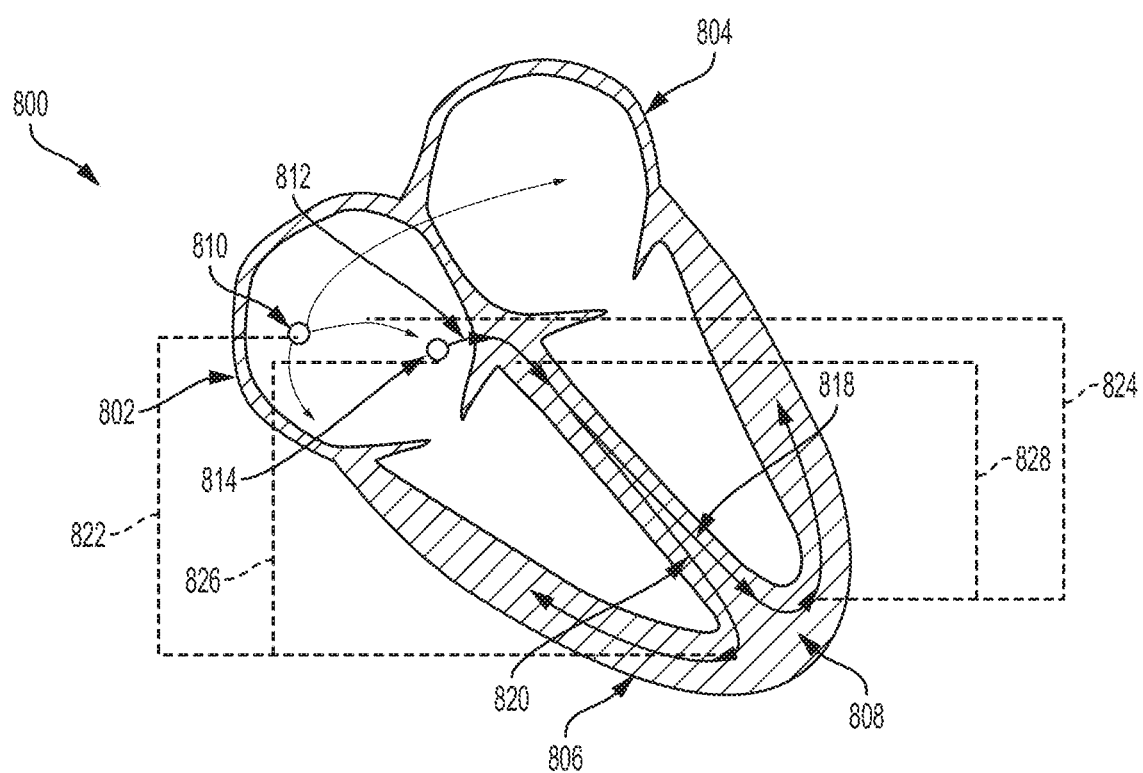
FIG. 8 shows an example of electrical pathways in a patient's heart.

FIG. 8 shows an example of electrical pathways in a patient's heart 800. As shown in FIG. 2, the heart 800 includes a right atrium (RA) 802, a left atrium (LA) 804, a right ventricle (RV) 806, a left ventricle (LV) 808, and an sinoatrial (SA) node 810 (including a propogating electrical signal extending from the SA node 810), HIS bundle 812, atrio-ventricular (AV) node 814, Left Bundle Branch (LBB) 818, and Right Bundle Branch (RBB) 820.

The SA node 810, the heart's natural pacemaker, generates intrinsic electrical pulses that propagate through an electrical conduction system to various regions of the heart to excite the myocardial tissues of the cardiac muscles. For example and as shown, intrinsic electrical pulses originating from the SA node 810 propagate through the AV node 814 between the RA 802 and RV 806. From the AV node 814, a specialized intrinsic conduction system is used by the electrical impulses to reach ventricular myocardial tissues, resulting in contraction activities of RV 806 and LV 808. A blocked or otherwise abnormal electrical conduction can cause the heart to contract dyssynchronously, resulting in poor hemodynamic performance that may diminish the amount of blood supplied to the heart and the rest of the body. For example, a block in conduction of the electrical pulses in either of the LBB 818 or the RBB 820 can cause dyssynchrony among the ventricles (RV 806 and LV 808) of the heart 808.

Coordinated delays of the propagations of the intrinsic electrical pulses in the conduction system of the heart 800 cause the various portions of the heart 800 to contract in synchrony which results in efficient pumping functions. Various aspects of the present disclosure are directed toward determining an optimal time interval from a sensed intrinsic atrial event to delivery of an electrical stimulation pulse, delivered by an implantable medical device as discussed above with reference to FIGS. 1-7, to a stimulation location in a His bundle of a subject (this can be referred to as paced atrial-His bundle delay, or paced AH delay (AHD) interval). Similarly, the heart 800 also includes an atrioventricular delay (AVD) for the heart 800 to contract in synchrony. As shown in FIG. 8, the electrical propagation delays of the heart 800 may specifically be broken down into a right atrioventricular delay (ARVD) 822, a left atrioventricular delay (ALVD) 824, a right ventricular-His bundle delay (HRVD) 826, and a left ventricular-His bundle delay (HLVD) 828.

Figure 9:
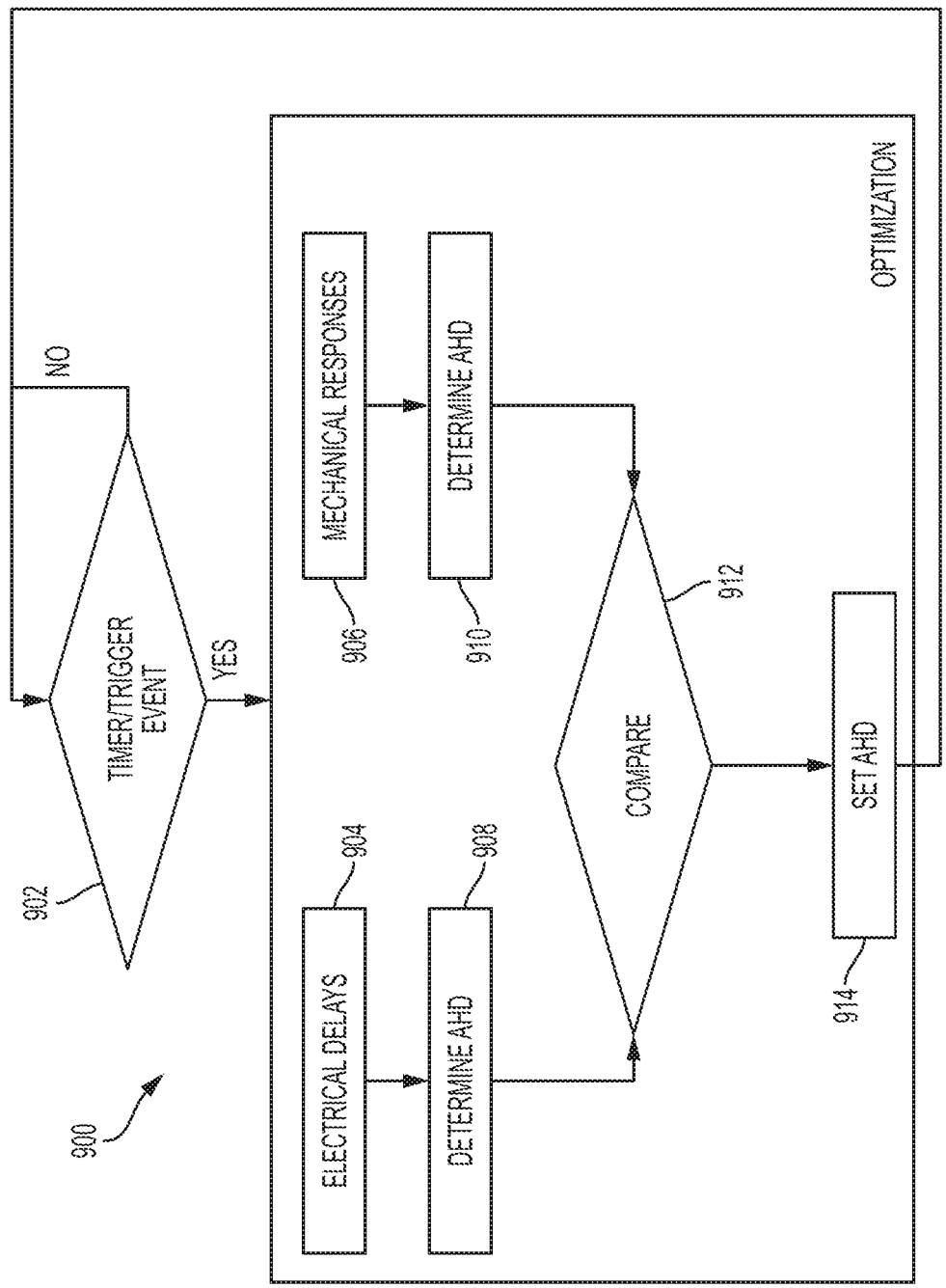
FIG. 9 shows a flowchart of an example His bundle pacing timing optimization that can be used in relation to embodiments of the present invention.

FIG. 9 shows a flowchart 900 of an example His bundle pacing timing optimization that can be used in relation to embodiments of the present invention. The flowchart 900 may be executed by circuitry contained in an implantable medical device or an external device that is communicatively coupled to the implantable medical device as discussed above with reference to FIG. 1. In certain instances, the His bundle pacing timing may be optimized based on the atrioventricular delay (AVD). A targeted or optimal delay equation for the implantable medical device to pace based on may be the AVD being equal to a first constant multiplied (e.g., a time delay) by the right atrioventricular delay (ARVD) added to a second constant multipled by a patient's heart QRS complex added to a third constant (AVD=k1*ARVD+k2*QRS+k3). Similarly and in certain instances, the optimal delay may be determined as a function of AHD, ARVD, ALVD, HRVD or HLVD, where the function can be linear or non-linear. The constants may be time delays.

In certain instances, the timing optimization of the bundle pacing may be based on mechanical responses or events of a patient's heart. Mechanical responses such as heart sounds may be sense using one or more electrodes (as discussed above), a pacing seed, an SCID lead, or other similar sensing mechanisms or LV pressure signals may be sensed by putting a sensor at the HIS bundle. The sensor may be arranged with a leady body as discussed above with reference to FIGS. 1-7.

As shown at block 902 in the flowchart 900 of FIG. 9, the His bundle pacing timing optimization may begin based on a timer or mechanical trigger event. If the timing or trigger event does not occur, the His bundle pacing timing executed by the implantable medical device is maintained based on the previously determined or set AHD (e.g., set prior to implantation, at implantation, or set previously based on the flowchart 900). When the timing or trigger event occurs, electrical delays (e.g., those discussed with reference to FIG. 8) are measured at block 904, and mechanical delays are measured at block 906. As shown at block 908 and block 910, optimal AHDs are determined based on electrical delays and mechanical delays respectively. The optimal AHDs may be determined based on at least one of HS/LV pressure signals, S1 amplitude, S2 amplitude, minimizing S1, S2 widths, minimizing the S2 split, minimizing S3, S4 amplitude, pre-ejection time, ejection time, LV end-diastolic pressure (LVEDP), LV contractility, and LV pulse pressure. In certain instances, the optimal AHD is the delay that can achieve maximum LV DPDT, S1 amplitude, S2 amplitude, or ejection time. In other instances, the optimal AHD is the delay that can achieve minimum S1, S2 widths, S3, S3 amplitudes, or pre-ejection time.

At block 912, the mechanically and electrically determined AHDs are compared. If the mechanically and electrically determined AHDs are equal, the equal AHD is communicated to the implantable medical device and set at block 914. If the mechanically and electrically determined AHDs are different, the mechanical response is set at block 914 if the difference between the mechanically and electrically determined AHDs is greater than a certain amount of time.

The set AHD may be impacted based on non-selective or selective capture of when the optimization occurs. In addition, sensor that may be used for determining a mechanical response may be a pressure sensor, a gyroscope, or an impedance sensor. In certain instances, a longer timing interval between the top of the RA to the HIS bundle location may indicate a great atrial dysynchrony. Thus, the HIS bundle pacing may be activated earlier than determined or calculated to facilitate atrial filing of the ventricles.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. An apparatus comprising:
   a lead body;
   a plurality of electrodes arranged with the lead body configured with a distal portion of the lead body having a bias configured to force the distal portion of the lead body against a tissue wall circumferentially about an area corresponding to a HIS bundle of a patient; and
   an implantable medical device coupled to the plurality of electrodes and configured to:
      convey electrical energy to one or more of the plurality of electrodes to stimulate a portion of the HIS bundle of the patient at a stimulation locus;
      analyze electrical signals via one or more of the plurality of electrodes in response to the conveyed electrical energy; and
      displace the stimulation locus based on the analyzed signals to pace the HIS bundle of the patient;
   wherein the distal portion of the lead body forms a spiral with the plurality of electrodes arranged with the spiral and the plurality of electrodes are directed toward a tissue wall about the HIS bundle; and
   wherein the lead body includes a bias portion configured to stabilize the plurality of electrodes of the spiral against the tissue wall of the HIS bundle.

2. The apparatus of claim 1, wherein the implantable medical device is configured to activate two or more of the electrodes to displace the stimulation locus between the plurality of electrodes.

3. The apparatus of claim 1, wherein the distal portion of the lead body includes one or more expandable tines, and the plurality of electrodes are arranged on the one or more expandable tines.

4. The apparatus of claim 1, wherein the distal portion of the lead body includes one or more wings extending outwardly from the distal portion relative to an end portion of the lead body, and the plurality of electrodes are arranged on at least one of the one or more wings and the end portion of the lead body.

5. The apparatus of claim 1, wherein the distal portion of the lead body includes one or more expandable balloon portions, and the plurality of electrodes are arranged with the one or more expandable balloon portions.

6. The apparatus of claim 1, wherein an end portion of the lead body includes the plurality of electrodes, and the plurality of electrodes are segmented by an insulative material.

7. The apparatus of claim 1, further comprising a fixation helix arranged at a distal end of the lead body, the fixation helix configured to anchor the lead body to the tissue wall about the HIS bundle.

8. The apparatus of claim 7, wherein the fixation helix is one of the plurality of electrodes.

9. The apparatus of claim 1, wherein the implantable medical device is configured to pace the HIS bundle of the patient based on a comparison of an electrical delay of an atrial-His bundle (AH) delay and a mechanical response of a portion of a heart of the patient.

10. The apparatus of claim 9, further comprising a lead body coupled to the implantable medical device and a sensor arranged with the lead body, and the sensor is configured to determine the mechanical response.

11. A system comprising:
    a plurality of electrodes arranged with a lead body configured with a distal portion of the lead body having a bias configured to force the distal portion of the lead body against a tissue wall circumferentially about an area corresponding to a HIS bundle of a patient;
    an implantable medical device coupled to the plurality of electrodes and configured to convey electrical energy to one or more of the plurality of electrodes to stimulate a portion of the HIS bundle of the patient at a stimulation locus and displace the stimulation locus to pace a HIS bundle of a patient; and
    an external programmer configured to receive the signals from the implantable medical device, analyze electrical signals via one or more of the plurality of electrodes in response to the conveyed electrical energy and transmit stimulation parameters to the implantable medical device to define the displacement of the stimulation locus;
    wherein the distal portion of the lead body forms a spiral with the plurality of electrodes arranged with the spiral and the plurality of electrodes are directed toward a tissue wall about the HIS bundle; and
    wherein the lead body includes a bias portion configured to stabilize the plurality of electrodes of the spiral against the tissue wall of the HIS bundle.

12. The system of claim 11, wherein the plurality of electrodes are separated by an insulative material to direct the electrical energy toward the HIS bundle of the patient.

13. The system of claim 11, wherein the distal portion of the lead body forms a curvature, and the distal portion includes a bias configured to stabilize the plurality of electrodes against a tissue wall of the HIS bundle.

14. The system of claim 11, wherein the distal portion of the lead body includes one or more expandable portions, and the plurality of electrodes are arranged on the one or more expandable portions.

15. The system of claim 11, wherein the expandable portions include at least one of expandable tines, expandable wings, and an expandable balloon.

16. A method of pacing a HIS bundle of a patient, the method comprising:
    arranging a plurality of electrodes at a HIS bundle of a patient, the plurality of electrodes being arranged with a lead body configured with a distal portion of the lead body having a bias configured to force the distal portion of the lead body against a tissue wall circumferentially about an area corresponding to a HIS bundle of a patient;
    conveying electrical energy to one or more of the plurality of electrodes to stimulate a portion of the HIS bundle of the patient at a stimulation locus;

analyzing electrical signals via one or more of the plurality of electrodes in response to the conveyed electrical energy; and displacing the stimulation locus based on the analyzed signals to pace the HIS bundle of the patient;

wherein the distal portion of the lead body forms a spiral with the plurality of electrodes arranged with the spiral and the plurality of electrodes are directed toward a tissue wall about the HIS bundle; and wherein the lead body includes a bias portion configured to stabilize the plurality of electrodes of the spiral against the tissue wall of the HIS bundle.

17. The method of claim 16, further comprising a implantable medical device and the plurality of electrodes are arranged with the lead body and further comprising directing the plurality of electrodes to apply the stimulation energy toward the HIS bundle using at least one of insulative material on the lead body and expandable portions arranged at the distal portion of the lead body.

18. The method of claim 17, wherein the expandable portions include at least one of expandable tines, expandable wings, and an expandable balloon, and wherein the plurality of electrodes are arranged with the expandable portions.

* * * * *